United States Patent [19]

Proctor

[11] Patent Number: 5,714,482
[45] Date of Patent: Feb. 3, 1998

[54] TOPICAL SPIN LABELS AND METHOD

[76] Inventor: Peter H. Proctor, 4126 Southwest Freeway, Ste. 1616, Houston, Tex. 77027

[21] Appl. No.: 464,411

[22] Filed: Jun. 5, 1995

Related U.S. Application Data

[63] Continuation-in-part of Ser. No. 229,374, Apr. 18, 1994, Pat. No. 5,470,876, and a continuation-in-part of Ser. No. 193,228, Feb. 7, 1994, Pat. No. 5,472,687, each is a continuation-in-part of Ser. No. 21,970, Feb. 24, 1993, Pat. No. 5,352,442, which is a continuation-in-part of Ser. No. 149,720, Jan. 29, 1988, abandoned, which is a continuation-in-part of Ser. No. 8,186, Jan. 28, 1987, abandoned, which is a continuation-in-part of Ser. No. 858,050, Apr. 30, 1986, abandoned, which is a continuation-in-part of Ser. No. 757,131, Jul. 18, 1985, abandoned.

[51] Int. Cl.$^6$ .................. A61K 31/555; A61K 31/40
[52] U.S. Cl. ........................... 514/190; 514/423
[58] Field of Search .................. 514/190, 423, 514/424, 398; 548/347.1, 349.1, 542, 537, 531

[56] References Cited

U.S. PATENT DOCUMENTS

| | | | |
|---|---|---|---|
| 2,409,754 | 10/1946 | Henze | 548/301 |
| 2,986,573 | 5/1961 | Topliss | 514/223.2 |
| 3,257,390 | 6/1966 | Patchett | 540/14 |
| 3,461,461 | 8/1969 | Anthony et al. | 544/323 |
| 3,527,864 | 9/1970 | MacMillen et al. | 425/59 |
| 3,551,554 | 12/1970 | Herschler | 424/7.1 |
| 3,896,238 | 7/1975 | Smith | 514/777 |
| 4,139,619 | 2/1979 | Chidsey, III | 424/45 |
| 4,189,039 | 2/1980 | Soldati | 544/12 |
| 4,254,145 | 3/1981 | Birnbaum | 424/305 |
| 4,344,941 | 8/1982 | Wiechert | 424/243 |
| 4,347,245 | 8/1982 | Shapiro | 424/241 |
| 4,367,227 | 1/1983 | Bingham | 514/178 |
| 4,444,762 | 4/1984 | Rajadhyaksha | 424/180 |
| 4,456,600 | 6/1984 | Wiechert | 424/238 |
| 4,596,812 | 6/1986 | Chidsey, III | 424/251 |
| 4,866,067 | 9/1989 | Di Schiena | 514/275 |
| 5,120,831 | 6/1992 | Pickart | 530/331 |
| 5,177,061 | 1/1993 | Pickart | 514/18 |
| 5,214,032 | 5/1993 | Pickart | 514/16 |
| 5,252,559 | 10/1993 | Kronholm | 514/18 |
| 5,256,678 | 10/1993 | Nakaguchi | 514/346 |

FOREIGN PATENT DOCUMENTS

| | | |
|---|---|---|
| 0027655 | 4/1981 | European Pat. Off. |
| 0249397 | 12/1987 | European Pat. Off. |
| 0273202 | 7/1988 | European Pat. Off. |
| 0327263 | 8/1989 | European Pat. Off. |
| 0415598 | 3/1991 | European Pat. Off. |
| 8022644 | 1/1996 | Japan |
| 2198132 | 6/1988 | United Kingdom |
| 8302558 | 8/1983 | WIPO |
| 8600616 | 1/1986 | WIPO |
| 8700427 | 1/1987 | WIPO |
| 9113619 | 9/1991 | WIPO |

OTHER PUBLICATIONS

Samuni et al, "SOD–Like Activity of 5–Membered Ring Nitroxide Spin Labels", CA 115:64685, 1991.
Anderson, Chemical Abstracts, vol. 90, p. 311K (1979).
Ando et al., Chemical Abstracts, 93:79872n (1980).
Bazzano et al., Journal of American Academy of Dermatology, vol. 15, pp. 880–883 (1986).
Berry, Pharmacology of the Skin, vol. 1, pp. 121–137 (1987).
Cheng et al., Archives of Dermatological Research, vol. 278, pp. 470–473 (1986).
Cumming et al., Journal of American Medical Association, vol. 247, pp. 1295–1298 (1982).
Current Therapy, pp. 599–603 (1984).
Dahl, Men's Fitness, pp. 93–95 (Feb. 1989).
Dawber, Dermatologica, vol. 175, suppl. 2, pp. 23–28 (1987).
DeVillez, Archives of Dermatology, vol. 121, pp. 197–202, (1985).
Dermatologica, vol. 175, suppl. 2, pp. 1–56 (Oct. 87).
Dostert et al., Xenobiotica, vol. 15, No. 10, pp. 799–803 (1985).
Ehman et al., Investigative Radiology, vol. 21, pp. 125–131 (1986).
Feelisch et al., Evr. Journal of Pharmacology, vol. 139, pp. 19–30 (1987).
Feelisch et al., Evr. Journal of Pharmacology, vol. 142, pp. 405–409 (1987).
Fiedler, Dermatologica, vol. 175, suppl. 2, pp. 29–35 (1987).
Fox et al., Annals of the New York Academy of Sciences, vol. 411, pp. 14–19 (1983).
Goffman et al., International Journal of Radiation, Oncology, Biology and Physics, vol. 22, pp. 803–806 (Nov. 4, 1992).
Headington, Current Therapeutic Research, vol. 36, pp. 1098–1105 (1984).
Hearse et al., Circulation Research, vol. 60, pp. 375–383 (1987).
Herschler, Chemical Abstracts, vol. 78, pp. 115239 (1973).
Ignarro et al., Biochemica et. Biophysica Acta, vol. 631, pp. 221–231 (1980).
J. Soc. Cosmetology Chem., (Italy) vol. 33, pp. 95–96 (Mar./Apr. 1982).

(List continued on next page.)

Primary Examiner—Deborah Lambkin
Attorney, Agent, or Firm—Daniel N. Lundeen; Sroufe, Payne & Lundeen, L.L.P.

[57] ABSTRACT

A composition and method for ameliorating a cellular dysfunction of a tissue such as the cosmetic treatment of hair loss and stimulation of hair growth are disclosed. The method comprises administering a spin label such as 2-(acetoxymercuri)-4,4,5,5-tetramethyl-2-imidazolin-1-yloxy-3-oxide, 3-carbamoyl-2,5-dihydro-2,2,5,5,-tetramethyl-1H-pyrrol-1-yloxy, or 3-([ethoxycarbonyl]-oxycarbonyl)-2,5-dihydro-2,2,5,5-tetramethyl-1H-pyrrol-1-yloxy to the affected tissue.

16 Claims, No Drawings

OTHER PUBLICATIONS

*Journal of American Medical Association*, vol. 260, No. 20 (1988).

Karlsson et al., *Journal of Cyclic Nucleotide and Protein Res.*, vol. 10, No. 4, pp. 309–315 (1985).

Kvedar, *Journal of American Academic Dermatology*, vol. 12, pp. 215–225 (1985).

*Longevity*, vol. 2, No. 3, p. 26 (Jan. 1988).

Lucky, *Archives of Dermatology*, vol. 121, pp. 57–62 (1985).

Messina, *Current Therapeutic Research*, vol. 34, pp. 319–324 (1983).

Messina, *Current Therapeutic Research*, vol. 38, pp. 269–282 (1985).

Mitchell et al., IBC USA Conference, South Natick, MA (Jun. 27, 1991).

Mittal et al., *Proc. of National Academy of Science*, USA, vol. 74, No. 10, pp. 4360–4364 (1977).

Palmer et al., *Nature*, vol. 327, pp. 524–526 (Jun. 11, 1987).

Parrett et al., *Journal of Pharmacology*, vol. 91, pp. 49–59 (1987).

*Physician's Desk Reference*, pp. 883, 977–978, 1782–1785, 1961 (1983).

Proctor et al., *Physiological Chemistry and Physics in Medical NMR*, vol. 16, pp. 175–195 (1984).

Ross, U.S. Department of Commerce, National Bureau of Standards, *Publication NSRDS–NBS59* (Jan. 1977).

Sekura, *Advances of Biology and Skin*, vol. XII, pp. 257–269, (1972).

Shapiro et al., *Journal of Clinical Endocrinology and Metabolism*, vol. 51, pp. 429–430 (1980).

Stewart, *International Journal of Dermatology*, vol. 17, pp. 167–179 (1978).

Thompson, *Federal Drug Administration Consumer*, pp. 10 and 12 (Mar. 10, 1981).

Tiffany–Castiglion, *Biochemical Pharmacology*, vol. 31, No. 2, pp. 181–188 (1982).

Torre (Ed.), *Annals of the New York Academy of Sciences*, vol. 411, Table of Contents (1983).

Vermorken, *Acta Dermatovener* (Stockholm), vol. 63, pp. 268–269 (1982).

Voorhees (Ed.), *Dermatologica*, vol. 175, suppl. 2, pp. 1–56 (1987).

Watanabe et al., *Archives of Dermatological Research*, vol. 278, pp. 470–473 (1986).

Weissmann, *Archives of Dermatology*, vol. 121, pp. 57–62 (1985).

Yoshioka et al. *Archives of Dermatological Research*, vol. 278, pp. 177–183 (1986).

Proctor, *Archives of Dermatology*, p. 1146 (Aug. 1989).

Gelvan et al., *Proc. of National Academy of Science*, USA, vol. 88, pp. 4680–4684 (1991).

Samuni et al., *Biochemistry*, vol. 30, pp. 555–561 (1991).

TOPICAL SPIN LABELS AND METHOD

CROSS-REFERENCE TO RELATED APPLICATIONS

This application is a continuation-in-part of applications Ser. No. 08/229,374, filed Apr. 18, 1994, now U.S. Pat. No. 5,470,876, and Ser. No. 08/193,228, filed Feb. 7, 1994 now U.S. Pat. No. 5,472,687 which are continuations-in-part of Ser. No. 08/021,970, filed Feb. 24, 1993, now U.S. Pat. No. 5,352,442; which is a continuation-in-part of Ser. No. 07/149,720, filed Jan. 29, 1988, abandoned; which is a continuation-in-part of application Ser. No. 07/008,186, filed Jan. 28, 1987, abandoned; which is a continuation-in-part of application Ser. No. 06/858,050, Apr. 30, 1986, abandoned; which is a continuation-in-part of application Ser. No. 06/757,131, Jul. 18, 1985, abandoned.

FIELD OF THE INVENTION

This invention relates to topical spin labels and a method for treating hair loss therewith.

BACKGROUND OF THE INVENTION

Several compounds have recently gained recognition for ameliorating cellular dysfunction. One type of dysfunction which has been well studied is alopecia for which anti-alopecia agents such as minoxidil and cyoctol have gained attention. However, most of these anti-alopecia agents are only minimally effective in some cases and/or can cause adverse dermatological or systemic reactions. Thus, the search continues for new, safer and more effective anti-alopecia agents as well as agents useful for treating other dysfunctionalities.

SUMMARY OF THE INVENTION

Applicant has discovered that certain spin labels have properties in the body for ameliorating cellular dysfunction in tissue attributed, in part, to high energy oxygen and hydroxyl free radicals, and enhancing recuperation of the tissue. The spin labels can be administered, for example, as an anti-alopecia agent to stimulate cosmetic hair growth, or as a protectant to minimize hair loss during cancer treatments known to induce hair loss.

DETAILED DESCRIPTION OF THE INVENTION

In the present invention, the spin label is compounded in a pharmaceutical formulation or carrier for topical or internal administration. The topical pharmaceutical carrier in which the spin label is generally substantially homogeneously dispersed can be an aqueous dispersion or suspension, or a water-in-oil or oil-in-water emulsion depending on the administration route. Topical pharmaceutical carriers which can be mentioned include water, urea, alcohols and glycols such as methanol, ethanol, propanol, butanol, ethylene glycol, propylene glycol, and the like. Internally administered pharmaceutical carriers typically include a sterile vehicle such as water or ethanol in which the spin label is suspended, dispersed or dissolved.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

Spin labels are typically used to study biomolecules which do not contain an unpaired electron. The spin label is a stable free radical which can be chemically bonded to the biomolecule of interest and produces a sharp and simple electron spin resonance (ESR) spectrum. The spin labels useful in the present invention include, for example, 2-(acetoxymercuri)-4,4,5,5-tetramethyl-2-imidazolin-1-yloxy-3-oxide, 3-carbamoyl-2,5-dihydro-2,2,5,5-tetramethyl-1H-pyrrol-1-yloxy, 3-([ethoxycarbonyl]-oxycarbonyl)-2,5-dihydro-2,2,5,5-tetramethyl-1H-pyrrol-1-yloxy and the like. These spin labels are commercially available.

Effective amounts of the spin label generally range from about 0.01 to about 20% by weight of the administered composition, more preferably from about 0.1 to about 10% by weight, most preferably from about 0.5 to about 3% by weight, but more or less can be present in the composition depending on the particular spin label formulation and the treatment conditions.

The spin label can be used alone or in combination with other additaments which are available to enhance the function of hair growth stimulation such as, for example, the hydroxyl radical scavengers, antiandrogens and others described in International Publication No. WO 87/00427 (International Application No. PCT/US86/01393) published on Jan. 29, 1987; and European Patent Application No. 89300785.6, Publication No. 0327263/A1, published Aug. 9, 1989; both of which are hereby incorporated in their entirety herein as though fully set forth verbatim, including reference therein to the publication of Ross & Ross, "Selected Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the spin label can be administered to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topically applied spin label is not limited thereto, however, and the stimulation of hair growth can include an increased rate of growth, increased hair diameter, follicular neogenesis, and the like; inhibiting hair loss or alopecia from progressing, for example, in male pattern baldness, or during the course of treatment with other therapeutic agents known to induce hair loss, such as chemotherapy or radiation therapy in cancer treatment. The spin labels can also be useful in ameliorating the rate of protein oxidation, DNA scission, cell viability loss, and the like in the tissue of internal organs such as the heart and brain; and ameliorating capillary loss, tissue atrophy characterized by a decrease in collagen and/or elastin and a decreased number, size and reproduction potential of fibroblasts, and strengthening the dermal-epidermal junction in skin; ischemic reperfusion injury secondary to myocardial infarction, stroke and surgical procedures; wound healing, for example, in burns and diabetic ulcerations; inflammatory and degenerative diseases such as rheumatoid arthritis, lupus and the like; fibrotic diseases such as Peyronie's disease, scarring, pulmonary fibrosis, and vitreous fibrosis; prevention of free-radical-induced vascular damage such as in atherosclerosis; other free radical diseases as outlined in Proctor et al., "Free Radicals and Disease in Man," *Physiological Chemistry and Physics and Medical NMR*, volume 16, pp. 175–195 (1984) which is hereby incorporated herein by reference; and the like.

The invention is illustrated by way of the following examples:

EXAMPLE 1

A spin label shampoo is prepared by mixing 0.5 g of a spin label in 500 ml of a commercially available shampoo. The shampoo is used daily on the scalp for normal shampooing of the hair for a period of from 3 to 6 months to obtain cosmetic hair growth.

EXAMPLE 2

A solution of spin label is prepared and used in the course of radiation treatment. A spin label, obtained commercially from Aldrich Chemical Company, is dissolved in 70 percent ethanol/30 percent water at a concentration of 70 mg/ml. Topical application of the solution is made prior to irradiation exposure at 20Gy to 50Gy. Hair loss in the treated spin label subjects is less severe and returns to normal more rapidly than in the control group similarly treated with the same ethanol/water solution without the spin label. Skin samples obtained from the treated group test positive for the presence of the spin label, while other tissue and blood specimens generally test negative. The application of the solution can also continue daily after the irradiation exposure. See Goffman, et al., "Topical Application of Nitroxide Protects Radiation-Induced Alopecia in Guinea Pigs," International Journal of Radiation Oncology, Biology and Physics, Volume 22, pp. 803–806, 1992, which is hereby incorporated herein by reference.

EXAMPLE 3

A 0.4 or 1 mM solution of a spin label is used to significantly reduce cardiac injury caused by reperfusion arrhythmia-ventricular fibrillation and ventricular tachycardia, as well as, post ischemic release of lactate dehydrogenase and OH.formation in isolated rat hearts subjected to regional ischemia. The rat hearts are obtained and perfused using a modified Krebs-Henseleit (KH) buffer, as detailed in Gelvan et al., "Cardiac Reperfusion Damage Prevented by a Nitroxide Free Radical," *Proceedings of the National Academy of Sciences*, USA, Medical Sciences, Vol. 88, pp. 4680–4684, June 1991, which is hereby incorporated herein by reference, in which a TEMPO solution was added to the perfusate. After reperfusion, heart function and resulting damage is analyzed. The spin label is found to strongly protect against reperfusion injury by preventing OH.formation rather than by decreasing heart rate or by direct suppression of arrhythmia.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

I claim:

1. A method for inhibiting the activity of oxygen and hydroxyl free radicals in an organism, comprising the step of:

administering a spin label selected from 2-(acetoxymercuri)-4,4,5,5-tetramethyl-2-imidazolin-1-yloxy-3-oxide, 3-carbamoyl-2,5-dihydro-2,2,5,5,-tetramethyl-1H-pyrrol-1-yloxy, and 3-([ethoxycarbonyl]-oxycarbonyl)-2,5-dihydro-2,2,5,5-tetramethyl-1H-pyrrol-1-yloxy to the tissue in an amount effective to inhibit the free radicals.

2. The method of claim 1, wherein the administration step is topical.

3. The method of claim 2, wherein the spin label is in the form of a dispersion, suspension or emulsion selected from creams, lotions, shampoos and cream rinses.

4. The method of claim 3, wherein the dispersion, suspension or emulsion comprises from about 0.01 to about 20 percent by weight of said spin label.

5. The method of claim 1, wherein the administration is internal.

6. The method of claim 1, wherein the spin label comprises 2-(acetoxymercuri)-4,4,5,5-tetramethyl-2-imidazolin-1-yloxy-3-oxide.

7. The method of claim 1 comprises 3-carbomoyl-2,5-dihydro-2,2,5,5-tetramethyl-1H-pyrrol-1-yloxy.

8. The method of claim 1 comprises 3-([ethoxycarbonyl]-oxycarbonyl)-2,5-dihydro-2,2,5,5-tetramethyl-1H-pyrrol-1-yloxy.

9. A topical pharmaceutical composition suitable for treating hair loss, comprising a spin label selected from 2-(acetoxymercuri)-4,4,5,5-tetramethyl-2-imidazolin-1-yloxy-3-oxide, 3-carbamoyl-2,5-dihydro-2,2,5,5,-tetramethyl-1H-pyrrol-1-yloxy, and 3-([ethoxycarbonyl]-oxycarbonyl)-2,5-dihydro-2,2,5,5-tetramethyl-1H-pyrrol-1-yloxy in association with a topical pharmaceutical carrier comprising an oil and water emulsion.

10. The topical pharmaceutical composition of claim 9, wherein the spin label comprises 2-(acetoxymercuri)-4,4,5,5-tetramethyl-2-imidazolin-1-yloxy-3-oxide.

11. The topical pharmaceutical composition of claim 9, wherein the spin label comprises 3-carbomoyl-2,5-dihydro-2,2,5,5-tetramethyl-1H-pyrrol-1-yloxy.

12. The topical pharmaceutical composition of claim 9, wherein the spin label comprises 3-([ethoxycarbonyl]-oxycarbonyl)-2,5-dihydro-2,2,5,5-tetramethyl-1H-pyrrol-1-yloxy.

13. A topical pharmaceutical composition suitable for treating hair loss comprising a spin label in association with a topical pharmaceutical carrier selected from creams, lotions, shampoos and cream rinses.

14. The topical pharmaceutical composition of claim 13, wherein the spin label comprises 2-(acetoxymercuri)-4,4,5, 5-tetramethyl-2-imidazolin-1-yloxy-3-oxide.

15. The topical pharmaceutical composition of claim 13, wherein the spin label comprises -carbomyl-2,5-dihydro-2, 2,5,5-tetramethyl-1H-pyrrol-1-yloxy.

16. The topical pharmaceutical composition of claim 13, wherein the spin label comprises 3-([ethoxycarbonyl]-oxycarbonyl)-2,5-dihydro-2,2,5,5-tetramethyl-1H-pyrrol-1-yloxy.

* * * * *